United States Patent
Catinat et al.

(10) Patent No.: US 6,169,050 B1
(45) Date of Patent: Jan. 2, 2001

(54) PROCESS FOR REGENERATION OF CATALYSTS OF TITANIUM SILICALITE TYPE

(75) Inventors: Jean-Pierre Catinat, Waudrez; Michel Strebelle, Brussels, both of (BE)

(73) Assignee: Solvay (Societe Anonyme) (BE)

( * ) Notice: Under 35 U.S.C. 154(b), the term of this patent shall be extended for 0 days.

(21) Appl. No.: 09/294,363

(22) Filed: Apr. 20, 1999

Related U.S. Application Data

(63) Continuation of application No. PCT/EP97/05685, filed on Oct. 9, 1997.

(30) Foreign Application Priority Data

Oct. 25, 1996 (BE) .................................................. 09600911

(51) Int. Cl.⁷ .............................. B01J 20/34; B01J 38/12
(52) U.S. Cl. ............................... 502/38; 502/34; 502/51; 502/53; 502/56
(58) Field of Search ................ 502/34, 38, 51, 502/53, 56

(56) References Cited

U.S. PATENT DOCUMENTS

| | | | |
|---|---|---|---|
| 5,262,550 | * 11/1993 | Crocco et al. | 549/531 |
| 5,306,682 | * 4/1994 | Ueda et al. | 502/52 |
| 5,384,418 | * 1/1995 | Zajacek et al. | 549/531 |
| 5,463,090 | * 10/1995 | Rodriguez et al. | 549/531 |
| 5,523,426 | * 6/1996 | Jubin, Jr. et al. | 549/531 |
| 5,527,984 | * 6/1996 | Cooker et al. | 204/428 |
| 5,591,875 | * 1/1997 | Chang et al. | 549/531 |
| 5,599,987 | * 2/1997 | Crocco et al. | 564/267 |
| 5,620,935 | * 4/1997 | Thiele | 502/22 |
| 5,646,314 | * 7/1997 | Crocco et al. | 549/531 |
| 5,675,026 | * 10/1997 | Thiele | 549/531 |
| 5,681,789 | * 10/1997 | Saxton et al. | 502/85 |
| 5,693,834 | * 12/1997 | Crocco et al. | 549/531 |
| 5,736,479 | * 4/1998 | Schodel et al. | 502/77 |
| 5,741,749 | * 4/1998 | Crocco et al. | 502/56 |

FOREIGN PATENT DOCUMENTS

| | | |
|---|---|---|
| 2 195 574 | 1/1997 | (CA) . |
| 44 25 672 A1 | 1/1996 | (DE) . |
| 0 100 119 | 2/1984 | (EP) . |
| 0 200 260 | 12/1986 | (EP) . |
| 0 376 453 | 7/1990 | (EP) . |
| 0 604 689 A1 | 7/1994 | (EP) . |
| 0 659 685 A1 | 6/1995 | (EP) . |
| 3-114536 | 5/1991 | (JP) . |

OTHER PUBLICATIONS

Grasselli, R.K. and Sleight, A.W. (Editors), *Structure–Activity and Selectivity Relationships in Heterogeneous Catalysis* (1991) Elsevier Science Publishers B.V., Amsterdam, pp. 243–255: Notari, "Titanium Silicalite: A New Selective Oxidation Catalyst".

Applied Catalysis A:General 92 (1992) Elsevier Science Publishing B.V., Amsterdam, pp. 93–111: Van Der Pol et al., "Parameters affecting the synthesis of titanium silicalite 1".

* cited by examiner

*Primary Examiner*—Tom Dunn
*Assistant Examiner*—Cam N. Nguyen
(74) *Attorney, Agent, or Firm*—Larson & Taylor, PLC

(57) ABSTRACT

The invention relates to a process for the regeneration of a catalyst of titanium silicalite type, used in particular in reactions for the oxidation of saturated hydrocarbons or for the epoxidation of olefins, by heat treatment under a gas stream.

11 Claims, No Drawings

PROCESS FOR REGENERATION OF CATALYSTS OF TITANIUM SILICALITE TYPE

This application is continuation of PCT/EP97/05685 filed Oct. 9, 1997.

FIELD OF THE INVENTION

The subject of the present invention is a process for the regeneration of catalysts of titanium silicalite type, which catalysts are used in particular in reactions between a peroxide compound, in particular hydrogen peroxide, and an organic coreactant.

BACKGROUND OF THE INVENTION

It is known to use a titanium silicalite as catalyst, in particular in oxidation reactions of saturated hydrocarbons in order to form alcohols or ketones, as described in European Patent Application EP-A-376,453, or in epoxydation reactions of olefins, as described in Patent Application EP-A-100,119, or alternatively in hydroxylation reactions of aromatic compounds, as reported in Application EP-A-200,260.

However, the activity of these catalysts rapidly falls. It consequently seems essential to have available a means for regenerating them in order to be able to use them repeatedly.

Patent Application JP 03/114536 describes a process for the regeneration of catalysts of titanium silicalite type by calcination under air at a temperature of 400 to 500° C. It is specified therein that a calcination at a temperature of less than 400° C. is insufficient for recovery of the initial catalytic activity of the catalyst.

SUMMARY OF THE INVENTION

The aim of the present invention is to provide a process for the regeneration of catalysts of titanium silicalite type which is more efficient than the known process and which can consequently be employed at a lower temperature.

The invention consequently relates to a process for the regeneration of a catalyst of titanium silicalite type comprising a heat treatment, which is characterized in that, during the heat treatment, the catalyst is stripped, at a temperature of at least 130° C., by a gas stream, the mass residence time of which on the catalyst does not exceed 2 hours.

By definition, the mass residence time of the gas stream on the catalyst is the ratio of the weight of catalyst to be regenerated to the mass flow rate of the gas stream. According to the invention, the mass residence time does not exceed 2 hours. Most often, it does not exceed 1 hour. Residence times of less than one minute can be envisaged. However, for practical reasons, the operation is generally carried out with a residence time of at least one minute. A mass residence time of 2 to 30 minutes has proved to be particularly advantageous.

The gas stream stripping the catalyst can contain any inert gas, such as nitrogen or helium. It can also contain an oxidizing gas, in particular oxygen. It can also contain steam. Preferably, the gas stream contains at least one compound chosen from nitrogen, oxygen and water.

DETAILED DESCRIPTION OF THE PREFERRED EMBODIMENT

The catalysts of titanium silicalite type to which the regeneration process according to the invention is applied are crystalline synthetic materials with a structure analogous to that of zeolites, comprising titanium and silicon oxides and characterized by an infrared absorption band at approximately 950–960 cm$^{-1}$. Their general formula is typically:

$$x\text{TiO}_2(1-x)\text{SiO}_2$$

in which x is between 0.0001 and 0.5, preferably between 0.001 and 0.05.

Materials of this type, known under the name of TS-1, exhibit a microporous crystalline zeolite structure analogous to that of zeolite ZSM-5. The properties and the main applications of these compounds are known (B. Notari; Structure-Activity and Selectivity Relationship in Heterogeneous Catalysis; R. K. Grasselli and A. W. Sleight Editors; Elsevier; 1991; p. 243–256). Their synthesis has also been widely studied (A. Van der Poel and J. Van Hooff, Applied Catalysis A; 1992; volume 92, pages 93–111). Other materials of this type have a structure analogous to that of beta-zeolite, zeolite ZSM-11 or zeolite MCM-41.

The heat treatment of the catalyst is generally carried out at a temperature of at least 150° C. A treatment temperature of at least 175° C. is preferred. Although the regeneration heat treatment according to the invention can be implemented up to a temperature of approximately 550° C., very good results can be obtained at a temperature of less than 400° C. In the presence of a substantial amount of water in the gas stream (at least 0.01 molar %), the process according to the invention provides excellent regeneration at a temperature of 175 to 250° C. The temperature is particularly from 180 to 220° C. In the substantial absence of steam in the gas stream, that is to say when the amount of water in the gas stream is less than 0.01 molar %, very good results have been obtained at a temperature of 250 to 350° C.

The optimum duration of the heat treatment depends on the state of deactivation of the catalyst to be regenerated. It is generally at least 30 minutes, preferably at least 1 hour. Most often, it does not exceed 20 hours. Good results have been obtained with a duration of treatment of 2 to 8 hours.

The heat treatment of the catalyst in the regeneration process according to the invention can be carried out by any appropriate means which produces stripping of the catalyst by the gas stream. It is possible, for example, to carry out the heat treatment in a rotary furnace equipped with a gas stripping system or in a stationary-bed or fluidized-bed reactor.

In a particularly preferred embodiment, the gas stream stripping the catalyst contains oxygen. In this embodiment, the oxygen content in the gas stream is at least 1 molar %. Preferably, it is at least 5 molar %. Although it is possible, in theory, to operate with a gas stream composed essentially of oxygen, the operation is usually carried out with a gas stream not containing more than 30 molar % of oxygen. The balance of the gas stream is then composed of other gases, such as nitrogen or steam. Excellent results have been obtained in the case where the gas stream is air.

In another particularly preferred embodiment, the gas stream stripping the catalyst contains a substantial amount of steam. In this embodiment, the water content in the gas stream is at least 0.01 molar %. Preferably, it is at least 0.05 molar %. It is possible to operate with a gas stream composed essentially of steam. However, excellent results are obtained with a gas stream containing less than 10 molar % of water. The balance of the gas stream is then composed of other gases, such as nitrogen or oxygen.

In an advantageous alternative form of this preferred embodiment, the gas stream stripping the catalyst contains oxygen, in addition to steam. Generally, the gas stream is composed essentially of moist air containing from 0.01 to 50 molar % of water. Advantageously, the gas stream is composed essentially of moist air containing from 0.01 to 10 molar % of water.

In an embodiment of the regeneration process according to the invention, the heat treatment is preceded by an operation in which the catalyst is washed with water or with an organic compound (which is preferably an alcohol, methanol being particularly preferred), in order to remove substantially all the compounds with which the catalyst was in contact in the reaction in which it was employed. The temperature of the washing liquid is generally between 25° C. and the boiling temperature of the washing liquid. This washing operation is carried out by bringing the catalyst into contact with water or with the organic compound for one or more periods of 5 minutes to 2 hours.

In an embodiment of the regeneration process according to the invention, the catalyst is subjected, before the heat treatment, to an operation in which it is stripped with an inert gas, usually nitrogen, at a temperature of 50 to 100° C. for a period of 10 minutes to 1 hour. The function of stripping the catalyst is to remove the volatile impurities from the catalyst.

In an alternative form, the catalyst can be subjected to the abovementioned washing and stripping operations.

The process according to the invention makes it possible repeatedly to restore virtually all the initial activity of the catalyst.

The process according to the invention applies to spent catalysts of titanium silicalite type, in particular those used in a reaction employing hydrogen peroxide and an organic coreactant, in particular those used in reactions for the epoxidation of olefins by means of hydrogen peroxide, for the hydroxylation of aromatic compounds or for the oxidation of saturated hydrocarbons. It applies more particularly to catalysts used in reactions for the epoxidation of olefins by means of hydrogen peroxide. It applies very particularly to catalysts used in the reaction for the epoxidation of allyl chloride to epichlorohydrin by means of hydrogen peroxide. In addition, the process can be applied to catalysts used in the reaction for the epoxidation of propylene to propylene oxide by means of hydrogen peroxide.

The invention is illustrated more fully in the following non-limiting examples.

EXAMPLE 1

7.7 grams of catalyst of titanium silicalite type TS-1 were placed in a 125 ml reactor equipped with a recirculation loop (total volume=250 ml). The reactor was continuously fed, at a flow rate of 250 ml/hour, with a solution of allyl chloride and of hydrogen peroxide in methanol (allyl chloride/$H_2O_2$=2 mol/mol; $H_2O_2$ concentration of 1.38 mol/kg) at a temperature of 36° C. The linear rate of passage of the solution recirculating through the reactor was adjusted to 1 m/min. The hydrogen peroxide concentration in the reaction mixture withdrawn was measured by iodometry. As soon as the degree of conversion of the hydrogen peroxide was 50% less than that obtained after operating for one hour, the reactor was emptied. The deactivated catalyst was washed with methanol circulating through the reactor in a loop system at a temperature of 35° C. After purging the reactor, the deactivated catalyst was transferred to a pyrex tube placed in an extracted oven. After having removed the volatile compounds from the catalyst by stripping the latter with nitrogen at a temperature of 75° C., the deactivated catalyst was subjected to a regeneration heat treatment at a temperature of 300° C. for 7 hours under a stream of dry nitrogen (water content less than or equal to 6 mg/$Sm^3$) at a flow rate of 200 Sl/h.

After cooling, the regenerated catalyst was again placed in the reactor for the epoxidation of allyl chloride and the reactor was again fed with the solution of allyl chloride and of hydrogen peroxide in methanol under the conditions set out above.

4 cycles, the same as that described above, of use/regeneration of the catalyst were carried out. At each cycle, the activity of the regenerated catalyst was measured by determining the amount of epichlorohydrin produced under these conditions before the degree of conversion of the hydrogen peroxide again falls by 25% with respect to its initial value measured after operating for one hour. Respective activities of 95, 98, 94 and 94 grams of epichlorohydrin were measured during these 4 cycles. By way of comparison, the activity of the fresh catalyst, that is to say when used for the first time, was 95 grams of epichlorohydrin.

EXAMPLE 2

11 cycles, the same as that described in Example 1, were carried out, the heat treatment for regeneration of the deactivated catalyst being implemented under a stream of nitrogen containing approximately 25 g of water per $Sm^3$ for 2.5 hours, everything else remaining unchanged.

During these eleven successive cycles of use/regeneration of the TS-1 catalyst, respective activities of 93, 97, 97, 95, 93, 94, 92, 93, 92, 91 and 94 grams of epichlorohydrin were measured.

EXAMPLE 3

8 cycles, the same as that described in Example 1, were carried out, the heat treatment for regeneration of the deactivated catalyst being implemented under a stream of air containing approximately 25 g of water per $Sm^3$ for 7 hours (cycles 1 and 2), 15 hours (cycles 3 and 6) or 5 hours (cycles 4, 5, 7 and 8), everything else remaining unchanged.

During these eight successive cycles, respective activities of 96, 99, 98, 98, 96, 97, 101 and 98 grams of epichlorohydrin were measured.

EXAMPLE 4

3 cycles, the same as that described in Example 1, were carried out, the heat treatment for regeneration of the deactivated catalyst being implemented at a temperature of 215° C. under a gas stream composed of nitrogen and of approximately 700 g of water per $Sm^3$, at a flow rate of 250 Sl/h, for 3.5 hours, everything else remaining unchanged.

During these 3 successive cycles, respective activities of 94, 93 and 92 grams of epichlorohydrin were measured.

EXAMPLE 5

4 cycles, the same as that described in Example 1, were carried out, the heat treatment for regeneration of the deactivated catalyst being implemented at a temperature of 200° C. under a stream of air containing 1 g of water per $Sm^3$, everything else remaining unchanged.

During these 4 successive cycles, respective activities of 91, 89, 91 and 91 grams of epichlorohydrin were measured.

EXAMPLE 6

Comparison

Example 5 was repeated, the heat treatment for regeneration of the deactivated catalyst being implemented under a stream of air containing 1 g of water per $Sm^3$ at a flow rate of 3 Sl/h, everything else remaining unchanged.

During the 4 successive cycles, respective activities of 83, 80, 75 and 72 grams of epichlorohydrin were measured.

EXAMPLE 7

2 cycles, the same as that described in Example 1, were carried out, the heat treatment for regeneration of the deactivated catalyst being implemented at a temperature of 155° C. under a stream of oxygen containing approximately 25 g of water per $Sm^3$ at a flow rate of 100 Sl/h, everything else remaining unchanged.

During these 2 successive cycles, respective activities of 84 and 85 grams of epichlorohydrin were measured.

EXAMPLE 8

Comparison

Example 7 was repeated, the heat treatment for regeneration of the deactivated catalyst being implemented at a temperature of 105° C., everything else remaining unchanged.

During the two successive cycles, respective activities of 78 and 71 grams of epichlorohydrin were measured.

What is claimed is:

1. Process for the regeneration of a spent catalyst of titanium silicalite resulting from a synthesis of an epoxide by reaction between an olefin and hydrogen peroxide, the process comprising heat treating the catalyst by stripping the catalyst at a temperature of at least 130° C. and less than 400° C. by a moving gas stream for a mass residence time from 1 minute to 1 hour.

2. Process according to claim 1, wherein the gas stream includes at least one components selected chosen from nitrogen, oxygen and water.

3. Process according to claim 1, wherein the gas stream includes oxygen.

4. Process according to claim 1, wherein the gas stream includes at least 0.01 molar % of water.

5. Process according to claim 1, wherein the treatment is carried out at a temperature of 150 to 350° C.

6. Process according to claim 1, wherein the treatment lasts from 30 minutes to 8 hours.

7. Process according to claim 1, wherein the catalyst results from the synthesis of epichlorohydrin by reaction between allyl chloride and hydrogen peroxide.

8. Process according to claim 1, wherein the catalyst results from the synthesis of propylene oxide by reaction between propylene and hydrogen peroxide.

9. The process according to claim 1 wherein the catalyst, farther comprising reusing the catalyst after said heat treating for synthesis of an epoxide by reaction between an olefin and hydrogen peroxide.

10. The process according to claim 9 wherein the epoxide comprises epichlorohydrin and the olefin comprises allyl chloride.

11. The process according to claim 9 wherein the epoxide comprises propylene oxide and the olefin comprises propylene.

* * * * *